US012521294B2

(12) United States Patent
Yang et al.

(10) Patent No.: US 12,521,294 B2
(45) Date of Patent: Jan. 13, 2026

(54) METHOD FOR CONTROLLING DEVICE FOR AUTOMATICALLY ADJUSTING AIRWAY OPENING BODY

(71) Applicant: The First Affiliated Hospital of Chongqing Medical University, Chongqing (CN)

(72) Inventors: Xiang-Mei Yang, Chongqing (CN); Min-Yue Sun, Chongqing (CN); Hong-Mei Chen, Chongqing (CN); Yan Luo, Chongqing (CN); Jun Wu, Chongqing (CN); Juan Huang, Chongqing (CN); Dong-Mei Li, Chongqing (CN); Qing Zeng, Chongqing (CN); Jing Zhou, Chongqing (CN); Jing Wen, Chongqing (CN); Jin-Jin Guo, Chongqing (CN)

(73) Assignee: The First Affiliated Hospital of Chongqing Medical University, Chongqing (CN)

( * ) Notice: Subject to any disclaimer, the term of this patent is extended or adjusted under 35 U.S.C. 154(b) by 482 days.

(21) Appl. No.: 17/985,918

(22) Filed: Nov. 14, 2022

(65) Prior Publication Data

US 2024/0099920 A1 Mar. 28, 2024

(30) Foreign Application Priority Data

Sep. 23, 2022 (CN) ........................ 202211165187.1

(51) Int. Cl.
*A61G 13/12* (2006.01)
*A61B 90/14* (2016.01)

(52) U.S. Cl.
CPC ............ *A61G 13/121* (2013.01); *A61B 90/14* (2016.02); *A61G 13/1215* (2013.01); *A61G 2203/42* (2013.01)

(58) Field of Classification Search
CPC .............. A61G 13/121; A61G 13/1215; A61G 13/1285; A61G 13/128; A61G 2203/42;
(Continued)

(56) References Cited

U.S. PATENT DOCUMENTS 2,386,134 A * 10/1945 Mermis ................. A61F 5/3707 5/632
10,799,412 B1 * 10/2020 Termanini ............ A61G 13/129
(Continued)

FOREIGN PATENT DOCUMENTS

CN 110279551 * 9/2019 ............. A61G 13/12

OTHER PUBLICATIONS

ProQuest translation of Wu et al, CN 110279551 (Year: 2019).*

*Primary Examiner* — Adam Baker

(57) ABSTRACT

A method for controlling a device for automatically adjusting an airway opening body position is provided. The device includes a horizontal base plate, a head support block, a back support plate, a neck support apparatus, a head cover assembly, and a programmable logic controller (PLC). The neck support apparatus is positioned between the head support block and the back support plate. The PLC is configured to controls a stroke of an electric cylinder according to the following equations: $\theta=1.235\beta+\alpha$, and $\alpha=KX+B+C$, where $\theta$ is a body position angle, the body position angle is an angle between a positive projection line of a connecting line from a mandibular angle to an external acoustic meatus on a symmetrical surface of a human body and the back support plate, and $\theta$ is a preset value ranging from 90° to 100°.

1 Claim, 5 Drawing Sheets

(58) Field of Classification Search
CPC . A61B 90/14–18; A61B 34/70; A61F 5/3707; A61F 5/3792; A61F 5/055; A61F 5/05891; A61F 5/05883; A61H 1/0292; A61H 1/0296
USPC .......................................................... 128/845
See application file for complete search history.

(56) References Cited

U.S. PATENT DOCUMENTS

| | | | | |
|---|---|---|---|---|
| 2013/0133137 | A1* | 5/2013 | Jackson ............... | A61B 6/0407<br>5/617 |
| 2016/0151222 | A1* | 6/2016 | Pedro .................... | A61M 16/06<br>128/203.29 |

* cited by examiner

METHOD FOR CONTROLLING DEVICE FOR AUTOMATICALLY ADJUSTING AIRWAY OPENING BODY

FIELD OF THE INVENTION

The present invention relates to medical equipment, and more particular to a device for adjusting an airway opening body position.

BACKGROUND OF THE INVENTION

Airway opening is the first step of tracheal intubation, cardiopulmonary resuscitation, tracheoscopy, etc. In tracheal intubation, body positions of a patient usually have three forms of a simple lean-back position, a sniffing position, and a ramped position. The simple lean-back position refers to that the head leans back naturally. It is mostly applied to infants and young children in general, and may also be applied to some visual laryngoscopes and other novel airway devices. The simple lean-back position is as shown in FIG. 1 of the specification. The sniffing position refers to that the neck is flexed via a bolster and then the head stretches backward. The sniffing position is as shown in FIG. 2 of the specification. At the sniffing position, a bending angle of the neck is 35° with respect to a horizontal plane, and a lean-back angle of the face is 15° with respect to the horizontal plane. To reach this angle, the head should be raised by 31-71 mm (an average value is 55 mm). The sniffing position is the most studied and widely used airway opening body position. The ramped position refers to that on the basis of maintaining the sniffing position, the upper half body of the patient is raised to cause the external acoustic meatus to be horizontally aligned with the sternal angle. The proposal of the ramped position is because raising the head of the obese patient alone cannot ensure that the obese patient is at the sniffing position. Due to the increase of the front and back chest diameters of the obese patient, it is almost impossible to bend the neck by 35°, unless the shoulder and neck are both raised to a certain position such that the obese patient can have the same mouth-pharynx-throat axis as the sniffing position of normal weight. A rough reference standard for opening the airway at the tamped position is to horizontally align the external acoustic meatus with the sternal angle.

To quickly and accurately open the patient's airway, the inventor has first developed a device for automatically adjusting an airway opening body position, and applied for a patent (patent number: ZL201910582372.2). In technology of the patent, a tilt angle sensor is arranged on a head cover, and a programmable logic controller (PLC) controls an electric cylinder to lift a neck support plate according to detection data fed back by the tilt angle sensor, to automatically open the patient's airway. In the technical solution of the patent, for the normal or thinner patient, an angle between a connecting line from the external acoustic meatus of the patient to the mandibular angle of the patient and a horizontal plane is used as a basis reference, and a first tilt angle sensor is arranged on the head cover to detect the angle. The technology is obtained on the basis of a sniffing position theory. For the obese patient, a relative height between the external acoustic meatus of the patient and the sternal angle of the patient is used as a basis reference, and a second tilt angle sensor is arranged on the head cover to detect the angle between the external acoustic meatus and the sternal angle of the patient and the angle between the external acoustic meatus and the horizontal plane. The technology is obtained on the basis of a ramped position theory.

However, in further practice and research, the inventor finds that there is still deficiency in satisfaction of opening the patient's airway by means of the sniffing position or the ramped position alone. Moreover, in the device for automatically adjusting the airway opening body position applied for by the inventor first, two tilt angle sensors need to be arranged on the head cover, so the structure of the head cover is more complicated, resulting in poorer wearing comfort.

SUMMARY OF THE INVENTION

In view of the defects existing in the prior art, an objective of the present invention is to provide a method for controlling a device for automatically adjusting an airway opening body position to integrate the advantages of a sniffing position and a ramped position, so as to better meet airway opening requirements of patients, simplify the structure of a head cover, and improve the wearing comfort of the head cover.

In the method for controlling the device for automatically adjusting the airway opening body position, the device for automatically adjusting the airway opening body position includes a horizontal base plate, a head support block, a back support plate, a neck support apparatus, a head cover assembly, and a programmable logic controller (PLC), where the neck support apparatus is positioned between the head support block and the back support plate;

- a straight guide rail is arranged on the horizontal base plate, and the head support block is arranged on the straight guide rail and is in sliding fit with the straight guide rail;
- the neck support apparatus includes a neck support plate with a groove in the middle, a flexible neck limit pad arranged in the groove, two guide columns that are fixed to the horizontal base plate and are respectively in up-down sliding fit with a left end and a right end of the neck support plate, a support seat arranged on the horizontal base plate, a lever having a middle part hinged to the support seat, a bracket arranged on the horizontal base plate, and an electric cylinder arranged on the bracket and having a telescopic rod facing down vertically, a first end of the lever is positioned below the neck support plate, a first sliding groove is formed in the first end of the lever, a first transmission pin penetrated in the first sliding groove is arranged at the bottom of the neck support plate, a second sliding groove is formed in a second end of the lever, a second transmission pin penetrated in the second sliding groove is arranged at an end of the telescopic rod of the electric cylinder, and an arc-shaped groove matched with the neck is formed in the flexible neck limit pad;
- a hinged shaft is arranged on a front side edge of the back support plate, a roller wheel rolling on the horizontal base plate is arranged on a back side edge of the back support plate, a vertical downward connecting rod is respectively fixedly connected to a left edge and a right edge of the neck support plate, and a lower end of the connecting rod is in running fit with the hinged shaft;
- the head cover assembly includes a head cover, a positioning plate arranged on the head cover, and a tilt angle sensor arranged on the positioning plate, and the positioning plate is configured to position a connecting line between an external acoustic meatus of a patient and a mandibular angle of the patient;

a signal input terminal of the PLC is connected to the tilt angle sensor, and a signal output terminal of the PLC is connected to the electric cylinder; and the PLC is configured to control a stroke of the electric cylinder according to the following equations:

$$\theta=1.235\beta+\alpha$$

$$\alpha=KX+B+C$$

wherein

θ is a body position angle, the body position angle is an angle between a positive projection line of the connecting line from the mandibular angle to the external acoustic meatus on a symmetrical surface of a human body and the back support plate, and θ is a preset value ranging from 90° to 100°;

β is a mandibular tilt angle, and the mandibular tilt angle is a Y-axis angle of the tilt angle sensor;

α is an angle between the back support plate and the horizontal base plate;

K is a lifting deviation coefficient of the neck support plate, and a value of K is constantly 0.303;

X is the stroke of the electric cylinder;

B is a height from the arc-shaped groove in the flexible neck limit pad to the horizontal base plate when the flexible neck limit pad is at an initial position, and a value of B is constantly 7.5; and C is a position deviation, and a default value thereof is 0.

The present invention has the following beneficial effects:

1. In the method for controlling the device for automatically adjusting the airway opening body position according to the present invention, the user-defined body position angle used includes an airway opening angle formed by flexion of the neck and backward stretching of the head and an airway opening angle formed by the patient lying on the back support plate, that is to say, the body position angle integrates a sniffing position and a ramped position, and the recommended range of the body position angle of 90° to 100° can meet airway opening requirements of most patients via experimental verification.
2. In the method for controlling the device for automatically adjusting the airway opening body position according to the present invention, only one tilt angle sensor needs to be arranged on the head cover of the device, such that the wearing structure of the head cover is simplified, thereby causing the head cover to be more comfortable to wear.

BRIEF DESCRIPTION OF THE DRAWINGS

The present invention will become more readily apparent to those ordinarily skilled in the art after reviewing the following detailed description and accompanying drawings, in which.

DETAILED DESCRIPTION OF PREFERRED EMBODIMENTS

Figure 1:
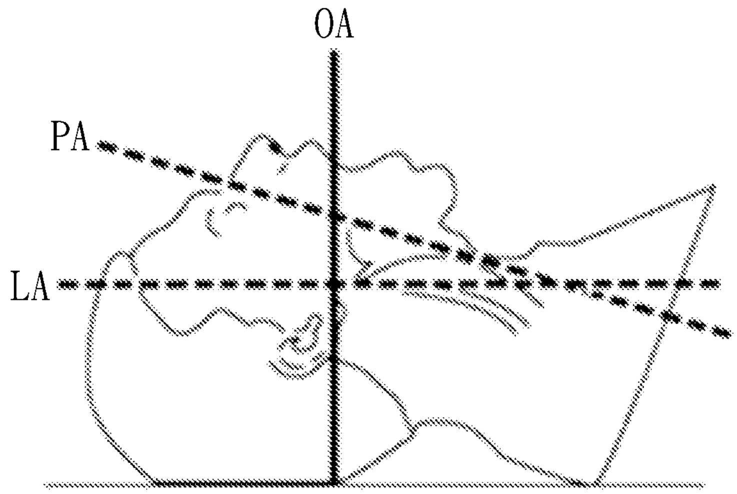
FIG. 1 is a schematic diagram of a simple lean-back position.
Figure 2:
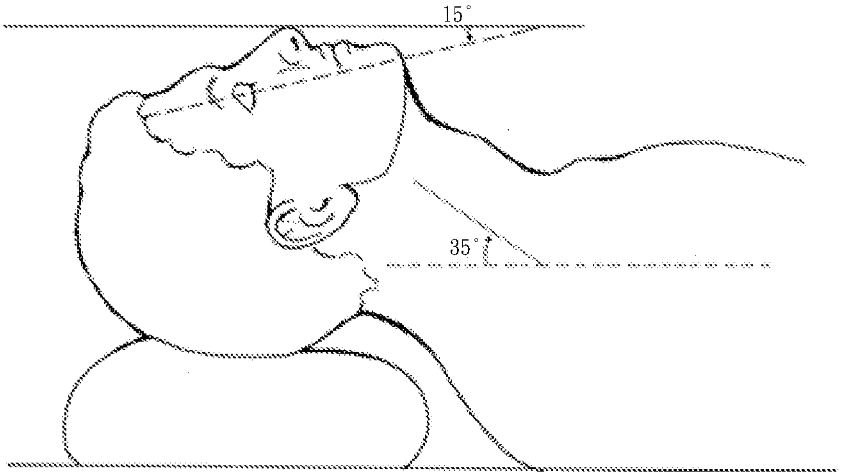
FIG. 2 is a schematic diagram of a sniffing position.
Figure 3:
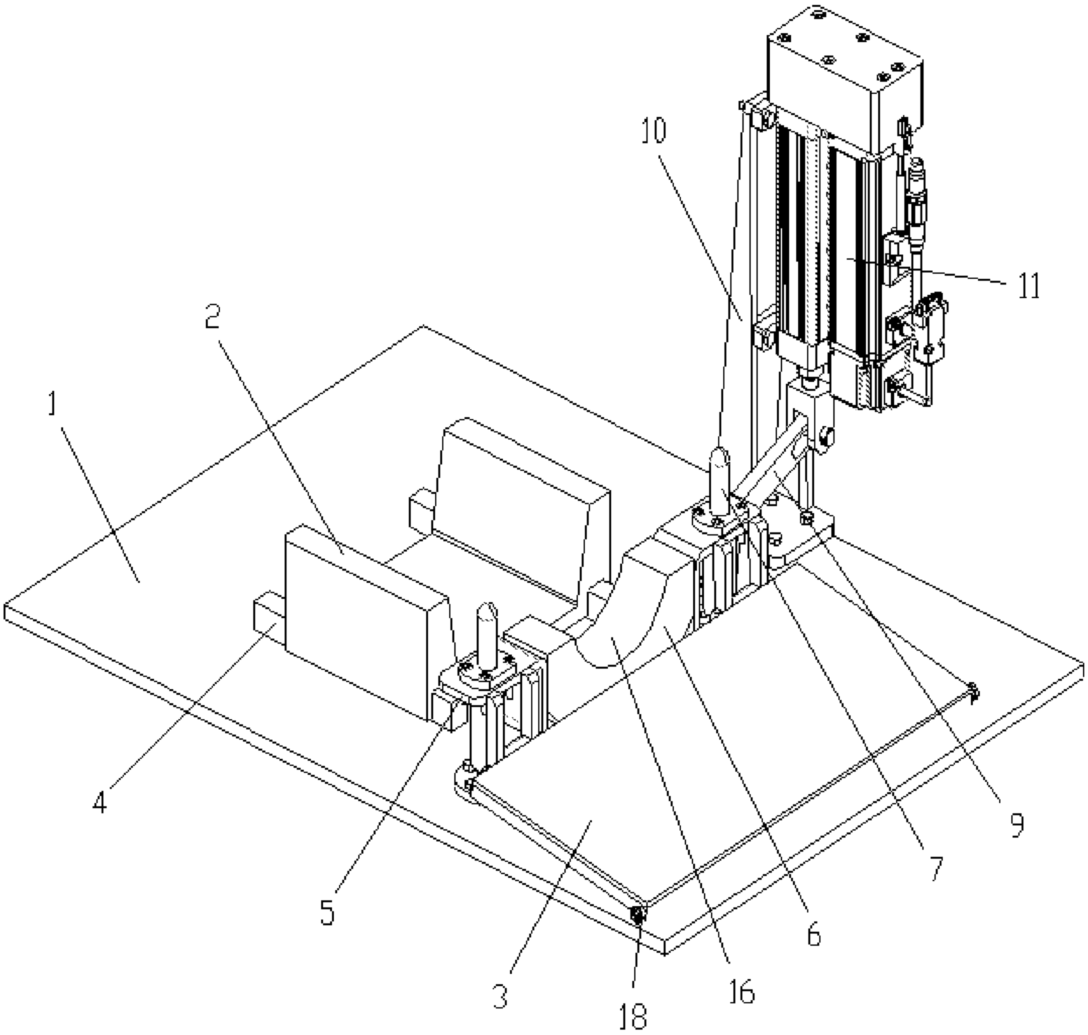
FIG. 3 is a schematic three-dimensional structural diagram of a device for automatically adjusting an airway opening body position in an embodiment.
Figure 4:
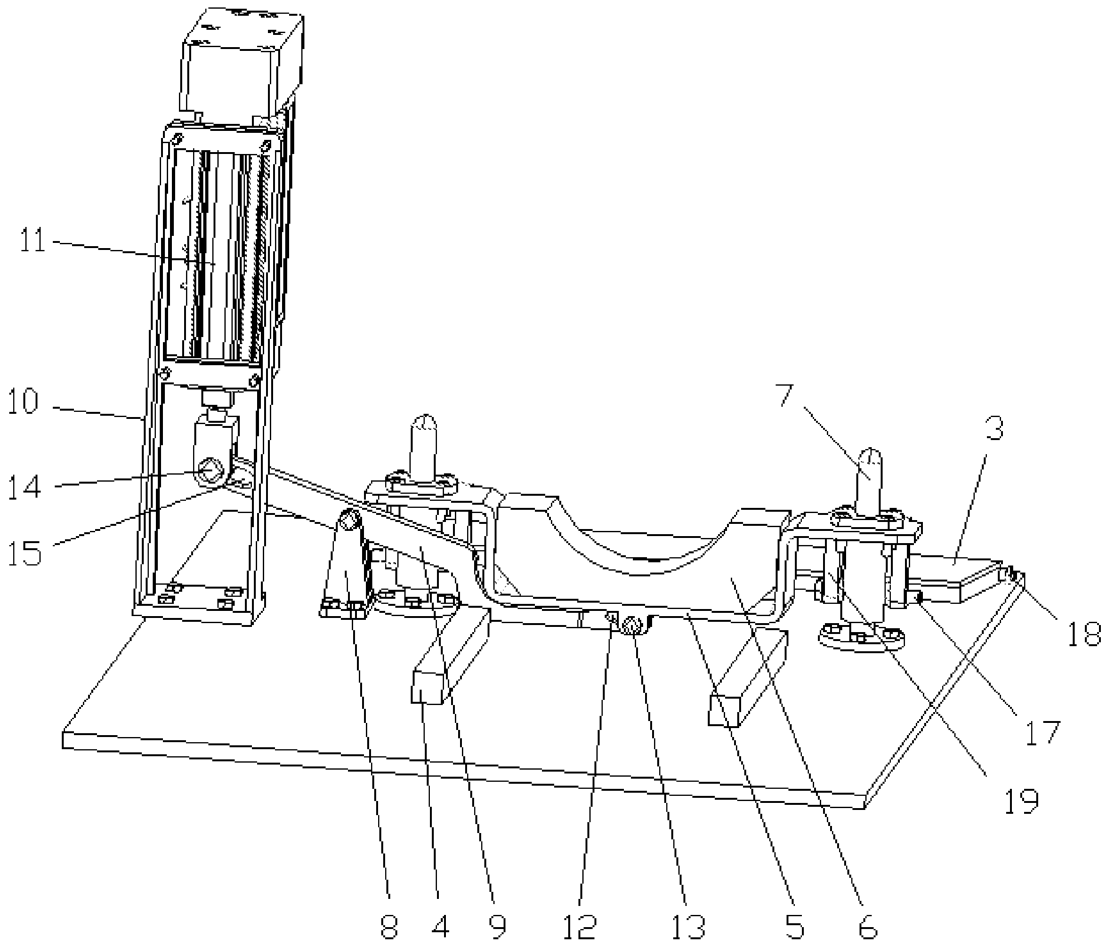
FIG. 4 is another schematic three-dimensional structural diagram of a device for automatically adjusting an airway opening body position in an embodiment.
Figure 5:
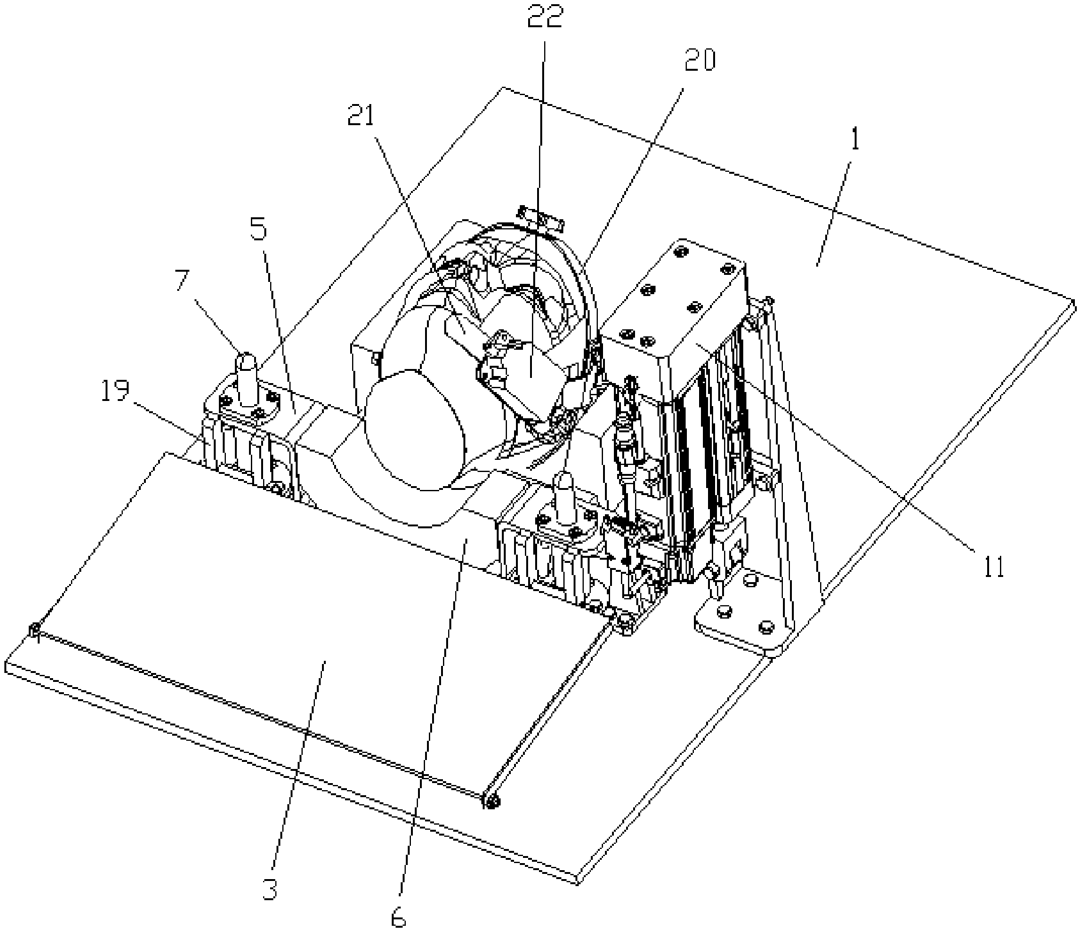
FIG. 5 is a schematic structural diagram of putting the head and neck on a device for automatically adjusting an airway opening body position.
Figure 6:
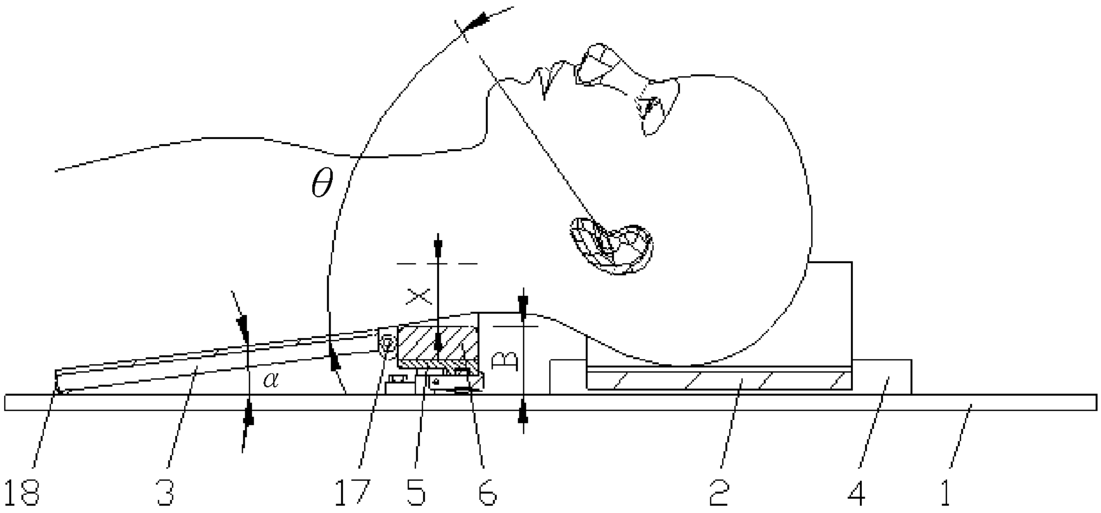
FIG. 6 is a schematic diagram of angles in equations.

The present invention is further described below in conjunction with the accompanying drawings and the embodiments.

In the method for controlling a device for automatically adjusting an airway opening body position according to this embodiment, the device for automatically adjusting the airway opening body position includes a horizontal base plate 1, a head support block 2, a back support plate 3, a neck support apparatus, a head cover assembly, and a programmable logic controller (PLC), where the neck support apparatus is positioned between the head support block and the back support plate.

A straight guide rail 4 is arranged on the horizontal base plate, and the head support block is arranged on the straight guide rail and is in sliding fit with the straight guide rail.

The neck support apparatus includes a neck support plate 5 with a groove in the middle, a flexible neck limit pad 6 arranged in the groove, two guide columns 7 that are fixed to the horizontal base plate and are respectively in up-down sliding fit with a left end and a right end of the neck support plate, a support seat 8 arranged on the horizontal base plate, a lever 9 having a middle part hinged to the support seat, a bracket 10 arranged on the horizontal base plate, and an electric cylinder 11 that is arranged on the bracket and has a telescopic rod facing down vertically. A first end of the lever is positioned below the neck support plate, and a first sliding groove 12 is formed in the first end of the lever. A first transmission pin 13 penetrated in the first sliding groove is arranged at the bottom of the neck support plate. A second sliding groove 14 is formed in a second end of the lever. A second transmission pin 15 penetrated in the second sliding groove is arranged at an end of the telescopic rod of the electric cylinder. An arc-shaped groove 16 matched with the neck is formed in the flexible neck limit pad.

A hinged shaft 17 is arranged on a front side edge of the back support plate. A roller wheel 18 rolling on the horizontal base plate is arranged on a back side edge of the back support plate. A vertical downward connecting rod 19 is respectively fixedly connected to a left edge and a right edge of the neck support plate. A lower end of the connecting rod is in running fit with the hinged shaft.

The head cover assembly includes a head cover 20, a positioning plate 21 arranged on the head cover, and a tilt angle sensor 22 arranged on the positioning plate. The positioning plate is configured to position a connecting line between an external acoustic meatus of a patient and a mandibular angle of the patient.

A signal input terminal of the PLC is connected to the tilt angle sensor, and a signal output terminal of the PLC is connected to the electric cylinder.

The PLC is configured to control a stroke of the electric cylinder according to the following equations:

$$\theta=A\beta+\alpha$$

$$\alpha=KX+B+C$$

wherein

θ is a body position angle, the body position angle is an angle between a positive projection line of the connecting line from the mandibular angle to the external acoustic meatus on a symmetrical surface of a human body and the back support plate, and θ is a preset value ranging from 90° to 100°.

β is a mandibular tilt angle, and the mandibular tilt angle is a Y-axis angle of the tilt angle sensor.

A is an angle conversion coefficient, and a value of A is constantly 1.235. Since the Y-axis angle of the tilt angle sensor is not on the symmetrical surface of the human body, it is needed to convert the Y-axis angle to a projection angle on the symmetrical surface of the human body.

α is a back plate tilt angle, and the back plate tilt angle is an angle between the back support plate and the horizontal base plate.

K is a lifting deviation coefficient of the neck support plate, and a value of K is constantly 0.303, obtained via experiments.

X is the stroke of the electric cylinder.

B is a height from the arc-shaped groove in the flexible neck limit pad to the horizontal base plate when the flexible neck limit pad is at an initial position, and a value of B is constantly 7.5.

C is a position deviation, and a default value thereof is 0.

In specific implementation, the PLC calculates the stroke X of the electric cylinder according to the preset angle θ, calculates the number of pulses that need to be emitted according to the stroke X, and sends a pulse signal to the electric cylinder according to the calculated number of pulses to control the stroke of the electric cylinder to reach X. During change of the stroke of the electric cylinder, the angle α between the back support plate and the horizontal base plate, and the mandibular tilt angle β will both change.

The following is an experiment of controlling the device for automatically adjusting the airway opening body position by means of the method mentioned in this embodiment to open the patient's airway.

360 patients who were examined or treated by an electronic bronchoscope in the pulmonary and critical care medicine of a level A tertiary hospital in Chongqing from Jan. 4, 2021 to Mar. 15, 2021 are selected by means of convenience sampling. According to a random sequence generated by a computer, a research assistant sequentially adjusts the body position angle of an instrument to 90° (referred to as an instrument group 90°), 95° (an instrument group 95°), or 100° (an instrument group 100°) to open the airway of a subject, then a clinician who has rich experience in bronchoscopic examination or treatment and was trained in advance uses the bronchoscope to enter the airway from the nose or oral cavity of the subject, and when the bronchoscope goes straight and observes the clearest glottic view of the subject after the epiglottis is seen, an electronic image of the glottic view is acquired and saved by means of a bronchoscope image management system. After the image acquisition is completed, an operating doctor keeps the position and direction of an operating rod of the bronchoscope unchanged, and then the research assistant adjusts the remaining two angles according to random results to acquire the electronic image of the glottic view by the same process, that is to say, for each subject, the electronic image of the glottic view is randomly acquired for three times in total. After this step is completed, the research assistant no longer adjusts the angle, and the remaining operations are performed by the operating doctor according to the routine bronchoscopic diagnosis and treatment.

Besides, a safety test stage starts when the subject wears a head measurement and control device and ends with the bronchoscopic examination or treatment. After a validity test process is completed, the subject is subjected to subsequent routine bronchoscopic diagnosis and treatment in an angle state of the final random sequence, and safety verification of the instrument is completed in this state. After the end of research, two research observers evaluate the pain degree of the subject related to the instrument by means of visual analogue scale (VAS) scores, make telephone follow-ups immediately, 0.5 h, 1 h, 3 h, 6 h, 12 h, and 24 h after the end of research to observe whether the subject has adverse reactions related to the instrument, such as scalp pain, forehead skin redness, scalp numbness, and neck soreness, and the number of cases, and record the properties, degrees, start time, durations, end time, and corresponding treatment measures of the adverse reactions, the relationships between the adverse reactions and the instrument, etc.

Cormack-Lehane classification, CL classification for short, is classification of glottic view exposure first proposed by Cormack and Lehane in 1984. It is often used as golden criteria to objectively determine whether the laryngoscopy, the tracheal intubation, and the airway are difficult and the classes of their degrees. In this research, the glottic view exposure, which is a main outcome indicator of validity, of the subject under the bronchoscope after the airway is opened by using the instrument is determined by means of the CL classification. The classification criteria are specifically as follows: class I, where the glottis is fully exposed, and the anterior and posterior commissures are visible; class II, where the glottis is partially exposed, and only the posterior commissure is visible; class III, where only the tip of epiglottis or the epiglottis is visible, but the glottis cannot be exposed; and class IV, where the glottis and the epiglottis cannot be exposed. The class III or IV in the CL classification is considered to have difficulty in glottic view exposure and belongs to difficult airway. In this research, the results of all the acquired glottis electronic images are determined independently by three doctors (two anesthetists and one respiratory intensive care unit (RICU) doctor) who have intermediate professional titles or above and rich experience in tracheal intubation. If one determined results of the three doctors are inconsistent, the final results shall be determined by an expert team leader. In addition, the three doctors are further masked and do not know a sequence of image acquisition and corresponding subject identity information during result determination. During image result determination, there is only one subject's group number and its corresponding glottic view image (the image named 1, 2, or 3) to protect patient's privacy and avoid result bias.

The distribution of three groups of mandibular tilt angles, back plate tilt angles, body position angles, and back plate relative elevation values (i.e., the stroke of the electric cylinder) actually measured by the device for automatically adjusting the airway opening body position is as shown in Table 1 below.

TABLE 1

Distribution of measured values of three groups of instruments

| Parameter values | Instrument group 90° | Instrument group 95° | Instrument group 100° |
|---|---|---|---|
| Mandibular tilt angles (M, IQR, °) | 72.15 (68.70-75.25) | 72.20 (69.23-75.10) | 72.70 (70.30-75.28) |
| Back plate tilt angles (M, IQR, °) | 10.85 (7.50-14.60) | 15.85 (12.33-18.98) | 20.25 (17.40-22.98) |
| Body position angles (M, IQR, °) | 90.30 (90.10-90.60) | 95.10 (95.00-95.30) | 100.10 (99.90-100.30) |

TABLE 1-continued

Distribution of measured values of three groups of instruments

| Parameter values | Instrument group 90° | Instrument group 95° | Instrument group 100° |
|---|---|---|---|
| Back plate relative elevation values (M, IQR, mm) | 10.60 (0.00-22.58) | 26.60 (15.63-36.35) | 40.45 (31.53-49.10) |

The Kendall's W test analysis finds that three clinicians have better consistency in three groups of CL classification determination results, Kendall's W coefficients are about 0.700, and P values are less than 0.001, seeing Table 2.

TABLE 2

Consistency test results of three doctors on three groups of CL classification determination results

| Groups | Kendall's W coefficients | Statistics | P values |
|---|---|---|---|
| Instrument group 90° | 0.697 | 449.259 | <0.001 |
| Instrument group 95° | 0.721 | 464.984 | <0.001 |
| Instrument group 100° | 0.684 | 441.365 | <0.001 |

During a validity test stage in this experiment, 216 subjects successfully complete three groups of tests. The incidence of difficulty in glottic view exposure (CL class≥class III) is 2.8% when the angle of the instrument is 90°, it is 4.2% when the angle of the instrument is 95°, and it is 2.3% when the angle of the instrument is 100°. All the subjects successfully complete a bronchoscopic examination or treatment surgery. In 216 subjects, when the angle of the instrument is 90°, CL class of 180 subjects (83.3%) is class I, CL class of 30 subjects (13.9%) is class II, CL class of 5 subjects (2.3%) is class III, and CL class of 1 subject (0.5%) is class IV, where CL class of 3 subjects (1.4%) is optimized from class II to class I when the angle of the instrument is 95°, CL class of 8 subjects (3.7%) is optimized when the angle of the instrument is 100°, and CL class of 5 subjects (2.3%) is also improved when the angle of the instrument increases from 95° to 100°. There is no statistical significance of difference in CL classification proportion of the three groups ($\chi 2=1.942$, $P>0.05$). Experimental results are as shown in Table 3:

TABLE 3

Cormack-Lehane classification after completion of three groups of tests (n = 216)

| Groups | Cormack-Lehane classification I | II | III | IV | Statistics | P values |
|---|---|---|---|---|---|---|
| Instrument group 90° | 180 (83.3%) | 30 (13.9%) | 5 (2.3%) | 1 (0.5%) | $\chi^2 = 1.942$ | 0.379 |
| Instrument group 95° | 183 (84.7%) | 24 (11.1%) | 7 (3.2%) | 2 (1.0%) | | |
| Instrument group 100° | 188 (87.0%) | 23 (10.6%) | 4 (1.9%) | 1 (0.5%) | | |

In addition, most of CL classification results of 129 subjects only completing one group or two groups of tests are also class I or class II, seeing Table 4 and Table 5.

TABLE 4

Cormack-Lehane classification after completion of one group of tests (n = 55)

| Groups | Cormack-Lehane classification I | II | III | IV |
|---|---|---|---|---|
| Instrument group 90° (n = 30) | 20 (66.7%) | 9 (30.0%) | 1 (3.3%) | 0 |
| Instrument group 95° (n = 2) | 2 (100.0%) | 0 | 0 | 0 |
| Instrument group 100° (n = 23) | 22 (95.7%) | 1 (4.3%) | 0 | 0 |

TABLE 5

Cormack-Lehane classification after completion of two groups of tests (n = 74)

| Groups | Cormack-Lehane classification I | II | III | IV |
|---|---|---|---|---|
| Instrument groups 90° and 95° (n = 30) | 55 (91.7%) | 5 (8.3%) | 0 | 0 |
| Instrument groups 95° and 100° (n = 38) | 70 (92.1%) | 6 (7.9%) | 0 | 0 |
| Instrument groups 90° and 100° (n = 6) | 9 (75.0%) | 3 (25.0%) | 0 | 0 |

In this experiment, a total of 345 subjects complete a safety test, where 2 subjects are not interviewed due to loss of contact, so 343 subjects are included in statistical analysis. The overall compliance of the subjects is 99.4%, and the failure rate is 0.6%. The research results show that the duration of the safety test is 14.34±5.30 min (range of 7-65 min), it is not reported that 343 subjects have any adverse reactions related to the instrument immediately, 0.5 h, 1 h, 3 h, 6 h, 12 h, and 24 h after the end of research. The incidence of the adverse reactions is 0, and the VAS scores are 0.

It is found through the experiment that when the airway is opened at three angles of 90°, 95°, and 100° by means of the method for controlling the device for automatically adjusting the airway opening body position in this embodiment under the bronchoscope, CL class of most patients is class I or class II. It indicates that this control method can effectively open the patient's airway and obtain good glottic view, which is advantageous for the bronchoscope to enter the lower respiratory tract smoothly via the glottis and continuously keep the airway open. Moreover, within 24 h of follow-up after the end of experiment, it is not reported that 343 subjects have any adverse reactions related to the instrument and there are no concerns about the angle of the instrument in terms of safety.

Finally, it should be noted that the above embodiments are merely intended to illustrate rather than to limit the technical solution of the present invention. Although the present invention has been described in detail with reference to the preferred embodiments, those of ordinary skill in the art should understand that the technical solution of the present invention may be modified or equivalently substituted without departing from the objective and scope of the technical solution of the present invention, which should be covered in the scope of claims of the present invention.

What is claimed is:

1. A method for controlling a device for automatically adjusting an airway opening body position, the device for automatically adjusting the airway opening body position comprising a horizontal base plate, a head support block, a back support plate, a neck support apparatus, a head cover assembly, and a programmable logic controller (PLC), wherein the neck support apparatus is positioned between the head support block and the back support plate;

a straight guide rail is arranged on the horizontal base plate, and the head support block is arranged on the straight guide rail and is in sliding fit with the straight guide rail;

the neck support apparatus comprises a neck support plate with a groove in the middle, a flexible neck limit pad arranged in the groove, two guide columns fixed to the horizontal base plate and respectively in up-down sliding fit with a left end and a right end of the neck support plate, a support seat arranged on the horizontal base plate, a lever having a middle part hinged to the support seat, a bracket arranged on the horizontal base plate, and an electric cylinder arranged on the bracket and having a telescopic rod facing down vertically, a first end of the lever is positioned below the neck support plate, a first sliding groove is formed in the first end of the lever, a first transmission pin penetrated in the first sliding groove is arranged at the bottom of the neck support plate, a second sliding groove is formed in a second end of the lever, a second transmission pin penetrated in the second sliding groove is arranged at an end of the telescopic rod of the electric cylinder, and an arc-shaped groove matched with the neck is formed in the flexible neck limit pad;

a hinged shaft is arranged on a front side edge of the back support plate, a roller wheel rolling on the horizontal base plate is arranged on a back side edge of the back support plate, a vertical downward connecting rod is respectively fixedly connected to a left edge and a right edge of the neck support plate, and a lower end of the connecting rod is in running fit with the hinged shaft;

the head cover assembly comprises a head cover, a positioning plate arranged on the head cover, and a tilt angle sensor arranged on the positioning plate, and the positioning plate is configured to position a connecting line between an external acoustic meatus of a patient and a mandibular angle of the patient;

a signal input terminal of the PLC is connected to the tilt angle sensor, and a signal output terminal of the PLC is connected to the electric cylinder; and the PLC is configured to control a stroke of the electric cylinder according to the following equations:

$$\theta=1.235\beta+\alpha$$

$$\alpha=KX+B+C$$

wherein $\theta$ is a body position angle, the body position angle is an angle between a positive projection line of the connecting line from the mandibular angle to the external acoustic meatus on a symmetrical surface of a human body and the back support plate, and $\theta$ is a preset value ranging from 90° to 100°;

$\beta$ is a mandibular tilt angle, and the mandibular tilt angle is a Y-axis angle of the tilt angle sensor;

$\alpha$ is an angle between the back support plate and the horizontal base plate;

K is a lifting deviation coefficient of the neck support plate, and a value of K is constantly 0.303;

X is the stroke of the electric cylinder;

B is a height from the arc-shaped groove in the flexible neck limit pad to the horizontal base plate when the flexible neck limit pad is at an initial position, and a value of B is constantly 7.5; and C is a position deviation, and a default value thereof is 0.

* * * * *